(12) United States Patent
Galindo

(10) Patent No.: US 10,285,849 B2
(45) Date of Patent: May 14, 2019

(54) OSTOMY POUCH SUPPORT KIT, SYSTEM AND METHOD

(71) Applicant: NU-HOPE LABORATORIES, INC., Pacoima, CA (US)

(72) Inventor: Bradley J. Galindo, Pacoima, CA (US)

(73) Assignee: Nu-Hope Laboratories, Inc., Pacoima, CA (US)

( * ) Notice: Subject to any disclaimer, the term of this patent is extended or adjusted under 35 U.S.C. 154(b) by 135 days.

(21) Appl. No.: 15/309,441

(22) PCT Filed: Aug. 20, 2014

(86) PCT No.: PCT/US2014/051768
§ 371 (c)(1),
(2) Date: Nov. 7, 2016

(87) PCT Pub. No.: WO2015/171173
PCT Pub. Date: Nov. 12, 2015

(65) Prior Publication Data
US 2017/0181885 A1 Jun. 29, 2017

Related U.S. Application Data

(60) Provisional application No. 62/016,064, filed on Jun. 23, 2014, provisional application No. 61/990,702, filed on May 8, 2014.

(51) Int. Cl.
*A61F 5/449* (2006.01)

(52) U.S. Cl.
CPC .................................. *A61F 5/449* (2013.01)

(58) Field of Classification Search
CPC .......................... A61F 5/449; A61F 2005/4495
See application file for complete search history.

(56) References Cited

U.S. PATENT DOCUMENTS

| | | | | |
|---|---|---|---|---|
| 2,684,676 A | * | 7/1954 | Perry | A61F 5/445 604/344 |
| 3,351,061 A | * | 11/1967 | Nolan | A61F 5/445 604/336 |
| 3,398,744 A | * | 8/1968 | Hooper | A61F 5/445 604/340 |
| 3,898,990 A | * | 8/1975 | Nolan | A61F 5/443 119/654 |

(Continued)

*Primary Examiner* — Susan S Su
(74) *Attorney, Agent, or Firm* — Lance M. Pritikin

(57) ABSTRACT

An ostomy support system, retrofit kit and deployment method may involve an ostomy pouch subsystem, a belt ring and a belt. The ostomy pouch subsystem includes a pouch, a wafer and a junction portion therebetween. The belt ring includes a junction-engagement aperture and first and second lateral securement portions disposed laterally of the aperture. The belt ring is configured to be repeatedly placed into and out of mounted engagement with the ostomy pouch subsystem. When the belt ring is in such mounted engagement, the aperture is in receipt of the junction portion and axially retained between the pouch and wafer. The belt includes two end portions configured for securement to respective belt securement portions. One or both end portions may be releasably securable to its respective belt securement portion by way of hook and loop fastener surfaces. Methods are also provided to deploy the ostomy support system on a wearer.

14 Claims, 5 Drawing Sheets

(56) References Cited

U.S. PATENT DOCUMENTS

| | | | | |
|---|---|---|---|---|
| 4,109,657 A * | 8/1978 | Carrington | A61F 5/448 | 604/338 |
| 4,219,023 A * | 8/1980 | Galindo | A61F 5/445 | 604/344 |
| 4,723,952 A * | 2/1988 | Esposito | A61F 5/448 | 604/338 |
| 4,865,594 A * | 9/1989 | Thomas | A61F 5/4404 | 604/332 |
| 5,330,455 A * | 7/1994 | McKay | A61F 5/448 | 604/332 |
| 5,626,570 A * | 5/1997 | Gallo | A61F 5/449 | 2/49.2 |
| 5,653,701 A * | 8/1997 | Millman | A61F 5/4408 | 604/337 |
| 5,989,235 A * | 11/1999 | Quacquarella | A61F 5/448 | 604/332 |
| 7,540,861 B1 * | 6/2009 | Voto | A61F 5/443 | 604/343 |
| 7,935,097 B1 * | 5/2011 | Moore | A61F 5/449 | 604/333 |
| 2003/0023210 A1 * | 1/2003 | Bedard | A61F 5/445 | 604/332 |
| 2008/0132856 A1 * | 6/2008 | Worsoee | A41D 13/1254 | 604/343 |
| 2011/0178483 A1 * | 7/2011 | Oberholtzer | A61F 5/448 | 604/344 |
| 2014/0249494 A1 * | 9/2014 | Bird | A61F 5/445 | 604/344 |
| 2014/0276500 A1 * | 9/2014 | Scott | A61F 5/449 | 604/343 |
| 2015/0065971 A1 * | 3/2015 | Goldsmith | A61F 5/448 | 604/342 |
| 2015/0282541 A1 * | 10/2015 | Appeldoorn | A61F 5/449 | 2/247 |
| 2017/0348140 A1 * | 12/2017 | Riedel | A61F 5/449 | |

* cited by examiner

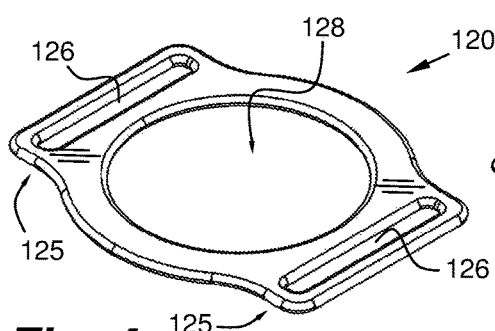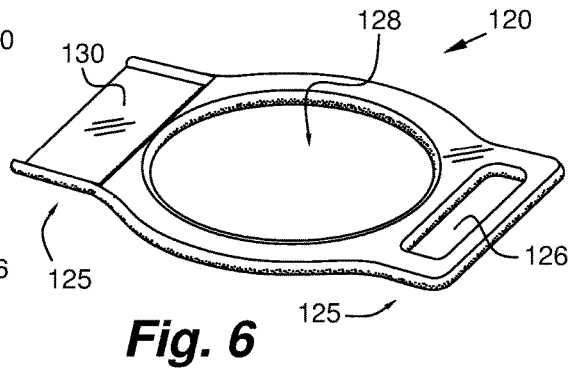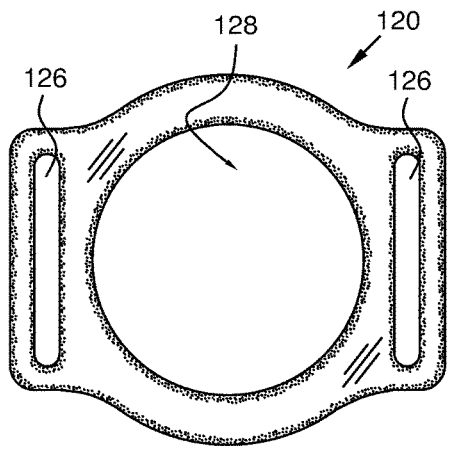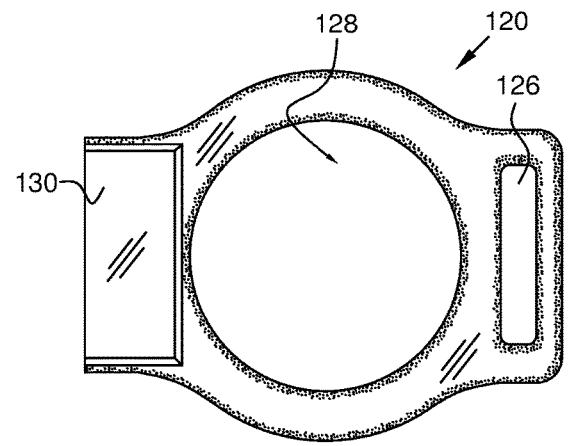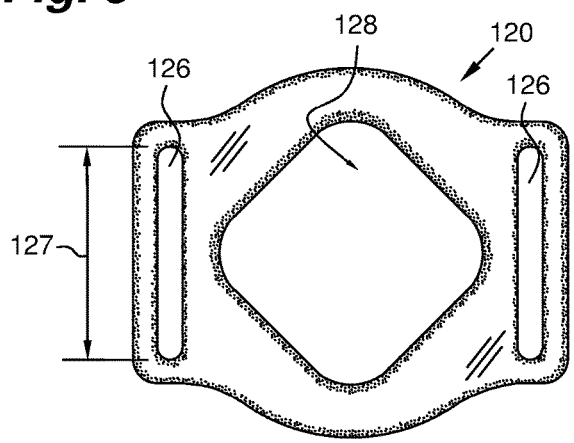

OSTOMY POUCH SUPPORT KIT, SYSTEM AND METHOD

RELATED APPLICATIONS

This application is a U.S. National Stage of International Application No. PCT/US2014/051768 filed Aug. 20, 2014, which claims the benefit of U.S. Provisional Application No. 61/990,702 filed May 8, 2014, and U.S. Provisional Application No. 62/016,064 filed Jun. 23, 2014, the contents of all of which are incorporated by this reference in their entireties for all purposes as if fully set forth herein.

TECHNICAL FIELD

The present invention relates to systems and methods for supporting urinary-diversion and fecal-diversion pouches.

BACKGROUND

Conventional ostomy pouches typically take the form of a one-piece system or a two-piece system. Both such systems include a pouch for collecting urine and/or stool, and a skin barrier. The skin barrier is a component that fits around the stoma to protect the skin and provide an interface which adheres the entire ostomy system to the wearer. In one-piece systems, the pouch is commonly welded (e.g., ultrasonically) to the skin barrier, creating what may be referred to as a "weld seal" (or "weld line") therebetween. In two-piece systems, the pouch and skin barrier (often called a "wafer") are attachable and separable from one another at a connection interface commonly referred to as a flange. A flange often takes the form of respective plastic rings residing on the pouch and the skin barrier that securely and sealingly engage with one another in repeatedly removable fashion. Two-piece ostomy systems are often favored because they allow pouches to be exchanged without requiring the wafer to be removed from the skin of the wearer. By way of example, certain wearers may prefer to temporarily switch to "mini pouch" for swimming, intimate or other short-term activities.

One of the most common methods of supporting ostomy pouches is to provide a belt that wraps around the wearer's abdomen and includes tabs which are attachable to small loops formed integrally with the flange interface of certain conventional ostomy pouches. Such belts may be used to help support the pouch. Further, such belts may be helpful in maintaining an adequate seal when using what is referred to in the ostomy industry as a "flat" or "convex" skin barrier.

SUMMARY

Certain deficiencies of the prior art may be overcome by the provision of one or more embodiments of kits, system and methods as discussed herein.

A support retrofit kit for an ostomy pouch subsystem having a pouch element, a wafer element and a junction portion may comprise a belt ring element. The belt ring element includes a junction-engagement aperture and first and second belt securement portions opposingly disposed laterally of the aperture. The belt ring element is preferably configured to being repeatedly placed in and removed from mounted engagement with the ostomy pouch subsystem, wherein the aperture is in receipt of the junction portion and is axially retained between the pouch element and wafer element. The junction portion may be a flange coupling or a weld joint. The junction portion may have a cross-section which is non-circular, and the junction-engagement aperture may have a shape which is complementary to the cross-section so as to restrict relative rotation between the belt ring element and the junction portion when the belt ring portion is in its mounted engagement. The kit may also preferably include an elastic belt element having first and second belt end portions configured for securement to respective belt securement portions of the belt ring. An ostomy support system may have, in assembled form, an ostomy pouch subsystem, a belt ring element and a belt element. Methods of deploying a compete ostomy support system on a wearer comprise a series of steps which ensure an average wearer is capable of quickly and easily assembling and using the ostomy support kits and systems discussed herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 4 is a diagrammatic perspective view of one non-limiting embodiment of a belt ring element in accordance with the present invention, including a pair of belt slots which are parallel to one another;

FIG. 5 is a diagrammatic plan view of the belt ring embodiment of FIG. 4;

FIG. 6 is a diagrammatic perspective view of an alternative non-limiting embodiment of a belt ring element in accordance with the present invention, illustrating a securement pad on one of the belt ring element at which to permanently affix one side of a respective belt end;

FIG. 7 is a diagrammatic plan view of the belt ring embodiment of FIG. 6;

FIG. 8 is a diagrammatic plan view of an embodiment similar to that of FIG. 5, but in which the junction-engaging aperture is non-circular;

DETAILED DESCRIPTION OF THE PREFERRED EMBODIMENTS

Figure 1:
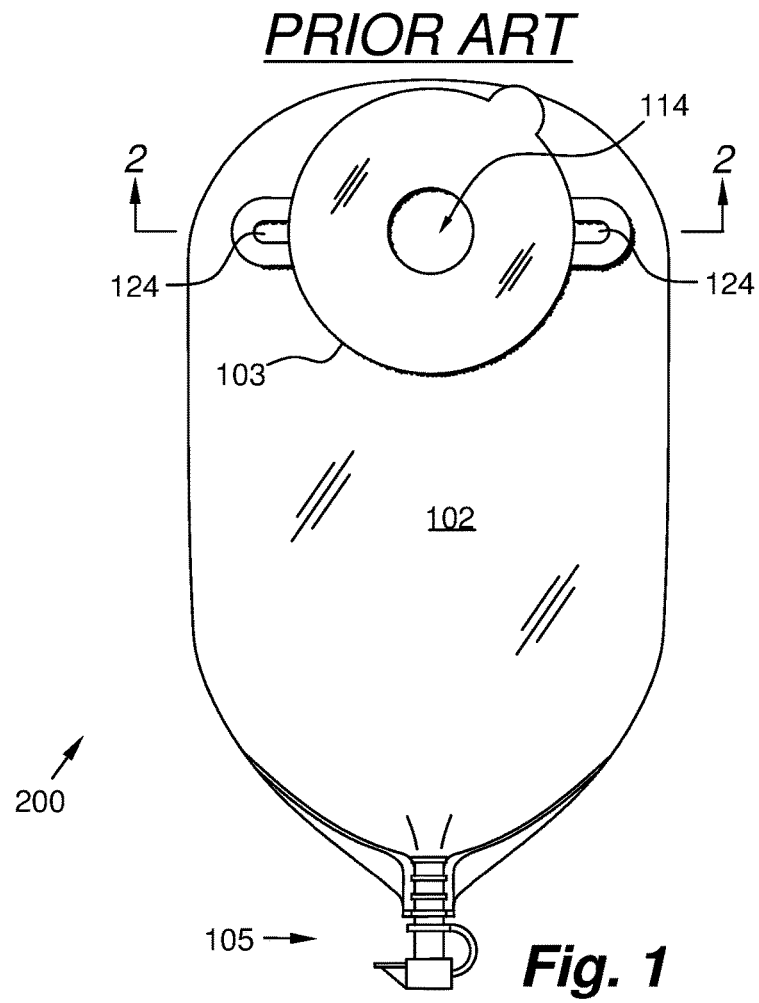
FIG. 1 is a diagrammatic plan view of one example of a common prior art ostomy pouch subsystem.

Referring now to the drawings, like reference numerals designate identical or corresponding features throughout the several views.

Figure 2:
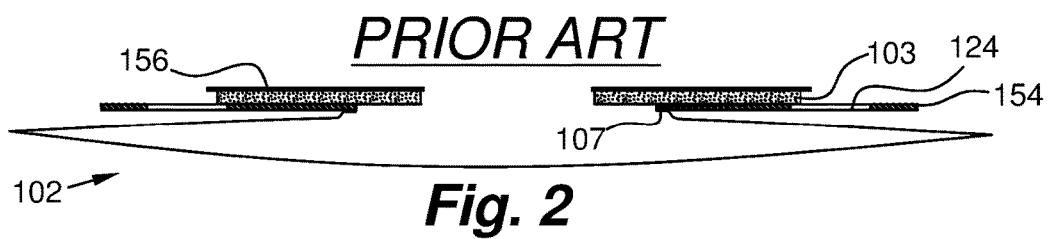
FIG. 2 is a diagrammatic cross-sectional view taken across lines 2-2 in FIG. 1.

Referring to FIGS. 11, 12, 14 and 17, for example, embodiments of a support retrofit kit 101 for an ostomy pouch subsystem 200 are illustrated. An ostomy pouch subsystem 200 may have a pouch element 102, a wafer element 103 and a junction portion 107 disposed connectingly therebetween. As illustrated for example in FIGS. 2 and 12, in a one-piece ostomy pouch subsystem the junction portion may take the form of a weld joint 134, conventionally or otherwise. Contrastingly, as illustrated for example in FIG. 14, in two-piece ostomy pouch subsystem the junction portion may take the form of a flange element 108.

Figure 12:
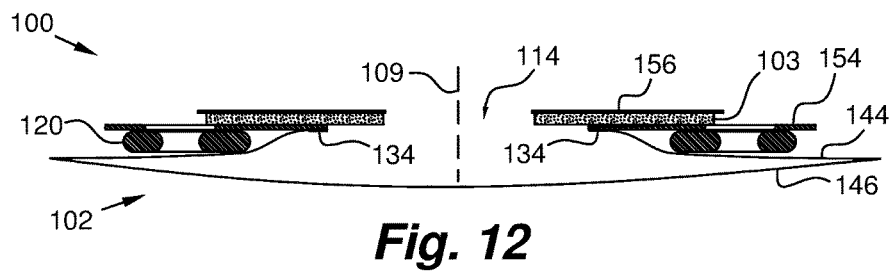
FIG. 12 is a diagrammatic cross-sectional view taken across lines 12-12 in FIG. 11, showing an embodiment of a belt ring element in mounted engagement with a one-piece ostomy pouch subsystem.
Figure 14:
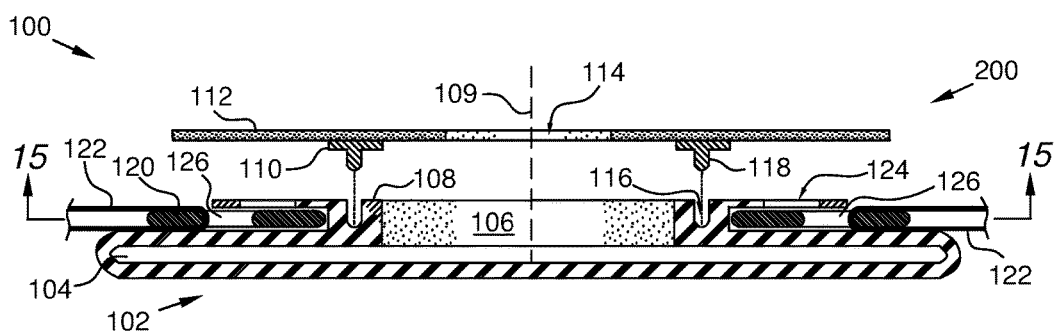
FIG. 14 is a diagrammatic cross-sectional view similar to that shown in FIG. 12, but showing an embodiment of a belt ring element in mounted engagement with a two-piece ostomy pouch subsystem.

Referring to FIGS. 4-8 and 17 for example, a support retrofit kit 101 in accordance with the present invention may preferably comprise a belt ring element 120 including a junction-engagement aperture 128 and first and second belt securement portions (see, for example reference characters 126 and 130) opposingly disposed laterally of the aperture 128. Referring to FIGS. 12 and 14 for example, the belt ring element 120 is preferably configured to being repeatedly placed in and removed from mounted engagement with the ostomy pouch subsystem 200. In such preferred embodiments, when the belt ring element 120 is in its mounted engagement, the junction-engagement aperture 128 is in receipt of the junction portion (for example weld line 134 or flange 108) and is axially retained between the pouch element 102 and the wafer element 103. Such axial retention may preferably happen along the axis 109, which runs normal to the stoma aperture 114.

Figure 17:
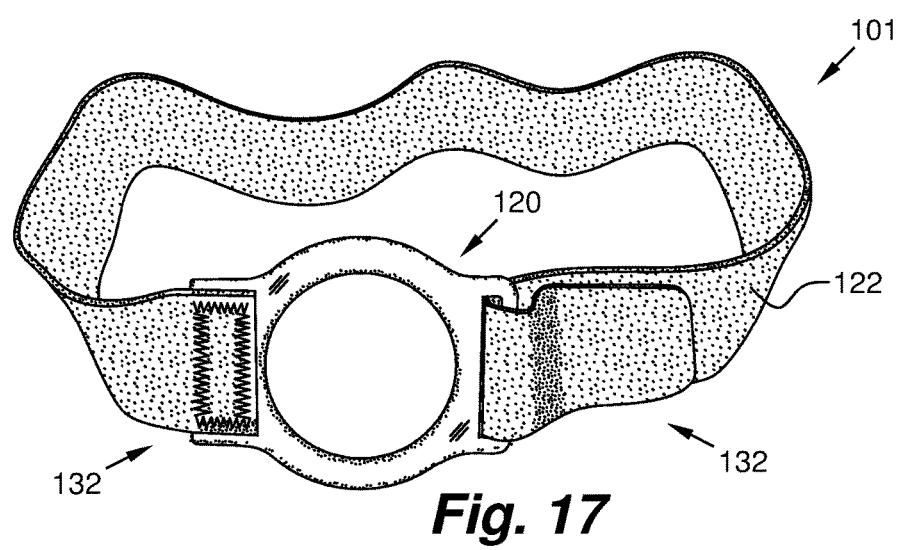
FIG. 17 is a diagrammatic perspective view of one non-limiting embodiment of a support retrofit kit in accordance with the present invention.
Figure 18:
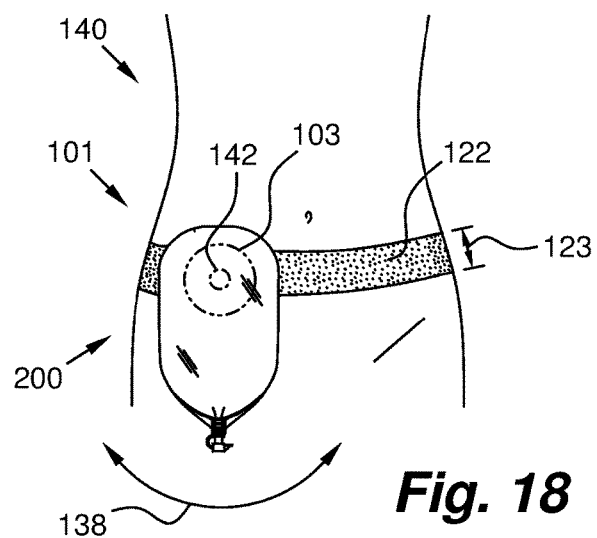
FIG. 18 is a diagrammatic front view of an ostomy support subsystem deployed on the torso of a wearer in accordance with one embodiment of the present invention.

Referring now to FIGS. 14, 17 and 18 for example, preferred embodiments of an ostomy support retrofit kit 101 further comprise a belt element 122 having first and second belt end portions 132 configured for securement to respective belt securement portions. In preferred embodiments, the belt element 122 is elastic to facilitate secure, comfortable, customized fit on the torso a wearer 140.

Referring to FIG. 12 for example, in certain embodiments the junction portion 107 is a weld joint 134 defined by the permanent sealed engagement between the pouch element 102 and the wafer element 103. Referring to FIG. 14 for example, in alternative embodiments, the junction portion 107 is a flange element 108 affixed to the pouch element 102 and adapted to releasably sealingly engage the wafer element 112. This releasable sealing engagement may be by way of, for example, coupling between a first seal engagement portion 116 and second seal engagement portion 118.

Figure 15:
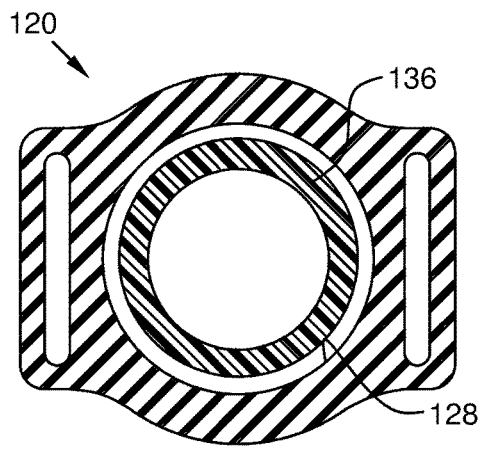
FIG. 15 is a diagrammatic cross-sectional view taken across lines 15-15 in FIG. 14, showing one example of a junction-engaging aperture and a junction portion cross section which are both circular.
Figure 16:
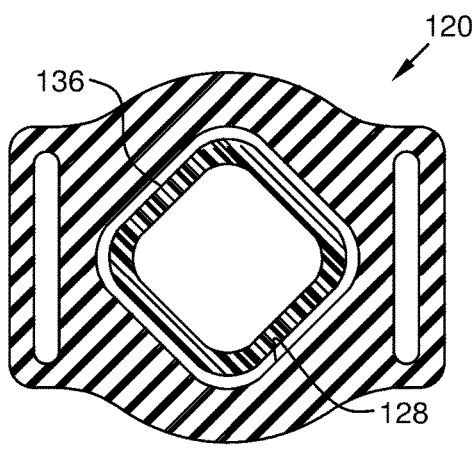
FIG. 16 is a diagrammatic cross-sectional view taken across lines 15-15 in FIG. 14, showing one example of a junction-engaging aperture and a junction portion cross section which are complementary to one another so as to restrict relative rotation between the belt ring element and the junction portion when the belt ring element is in mounted engagement with the respective ostomy pouch subsystem.

Referring to FIGS. 15 and 16 for example only, the junction portion 107 of the ostomy pouch subsystem may have a cross-section 136 which is circular (see for example, FIG. 15) or non-circular (see for example FIG. 16). Referring to FIGS. 16 and 18 for example, the junction-engaging aperture 128 may preferably have a shape which is complementary to the cross-section 136 so as to restrict relative rotation 138 between the belt ring element 120 and the junction portion 107 when the belt ring portion 120 is in its mounted engagement with the respective ostomy pouch subsystem 200. In certain such embodiments, the cross-section 136 may be, for example, polygonal or oval.

Referring to FIG. 18 for example, the belt element 122 may have a belt width 123. In particular embodiments, such as those illustrated in FIGS. 4, 5 and 8 for example, the belt securement portions 125 may each include an elongated slot 126 for receiving the belt element (for example, the end portions thereof) therethrough. In such embodiments, the elongated slots 126 may have a slot length 127 which is substantially the same as the belt width 123. More particularly, in certain such embodiments the belt slots 126 are preferably parallel to one another and the belt width 123 is between 85% and 100% of the slot length 127.

In certain embodiments, such as the one shown in FIG. 17 for example, one of the belt end portions 132 may preferably be permanently affixed to a respective one of the belt securement portions 125. Referring to FIG. 6, this may be accomplished for example where one of the belt securement portions 125 includes a securement pad 130 to which the respective belt end portion 132 is securement stitched (see FIG. 17 for example) or otherwise securely adhered. In such embodiments, the other belt end portion 132 may be releasably securable to its respective belt securement portion 125 by way of, for example, hook and loop fastener surfaces (such as Velcro®) or the like.

Exemplary embodiments of an ostomy pouch support system 100 may comprise an ostomy pouch subsystem 200, a belt ring element 120 and a belt element 122. The ostomy pouch subsystem 200 may have a pouch element 102, a wafer element 103 or 112, and a junction portion 107 therebetween. The belt ring element 120 may include a junction-engagement aperture 128 and first and second belt securement portions 125 opposingly disposed laterally of the aperture 128. The belt ring element 120 may be removably placed in mounted engagement with the ostomy pouch subsystem 200 wherein the aperture 128 is in receipt of the junction portion 107 (for example, weld joint 134 or flange 108) and is axially retained between the pouch element 102 and the wafer element 103 or 112. The belt element 120 may have first and second belt end portions 132 configured for securement to respective belt securement portions 125. At least one of the belt end portions may be releasably securable to its respective belt securement portion 125 by way of hook and loop fastener surfaces or the like.

Exemplary embodiments of a method of deploying an ostomy support system 100 on a wearer 140 may comprise one or more steps. A belt ring element 120 is selected which includes a junction-engagement aperture 128, first and second belt securement portions 125 opposingly disposed laterally of the aperture 128, and a belt element 122 having first and second belt end portions 132 configured for securement to respective belt securement portions 125. An ostomy pouch is provided (for example, chosen by a wearer, manufacturer, distributor or retailer) which has a pouch element 102, a wafer element 103 or 112 and a junction portion 107 (such as weld joint 134 or flange 108). Such an ostomy pouch may be of a conventional type, as illustrated for example in FIGS. 1-2. The belt ring element 120 is placed in mounted engagement with the ostomy pouch subsystem 200 whereby the junction-engagement aperture 128 is in receipt of the junction portion 107 and the belt ring element 120 is axially retained between the pouch element 102 and the wafer element 103 or 112. Referring to FIGS. 12 and 18 for example, a peel layer 156 may be removed from the wafer element and the wafer element 103 adhered to the skin of the wearer 140 in alignment about a stoma 142 which typically protrudes from the wall of the wearer's abdomen. The belt element 122 my then be wrapped around the torso of the wearer 140 and releasably secured thereat.

Figure 9:
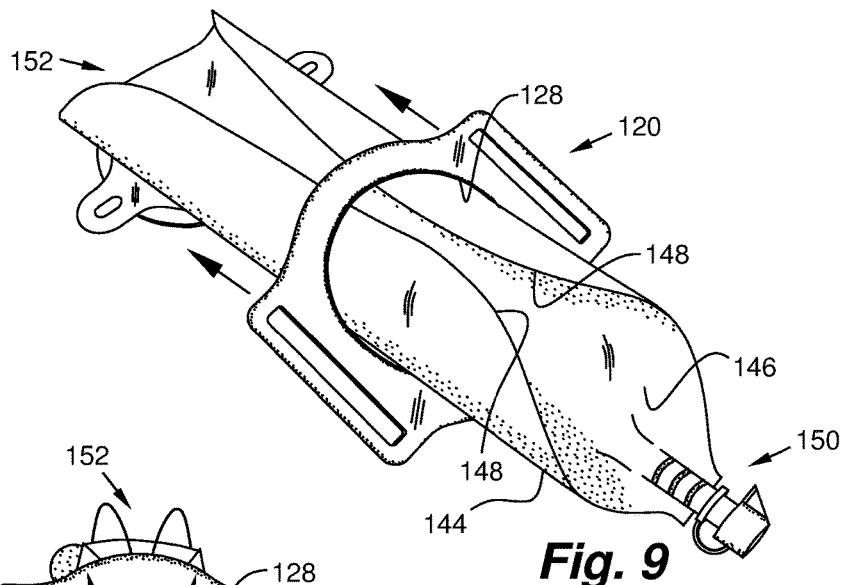
FIG. 9 is a diagrammatic perspective view of one or more an intermediate steps of an exemplary method of deploying an ostomy support system in accordance with the present invention, showing the lateral sides of the pouch folded toward one another over the outer face, the lower end of the pouch element being inserted into the junction-engaging aperture of the belt ring element, and the belt ring being slid toward the upper end of the pouch element.
Figure 10:
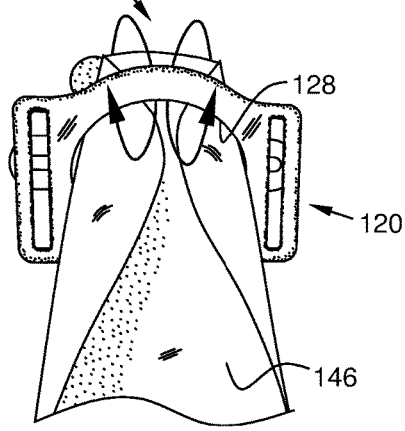
FIG. 10 is a diagrammatic perspective view of an exemplary subsequent step to the one or more steps depicted in FIG. 9, showing the belt ring element having reached the upper end of the pouch element and the upper end of the pouch element about to be fed through the junction-engagement aperture.
Figure 11:
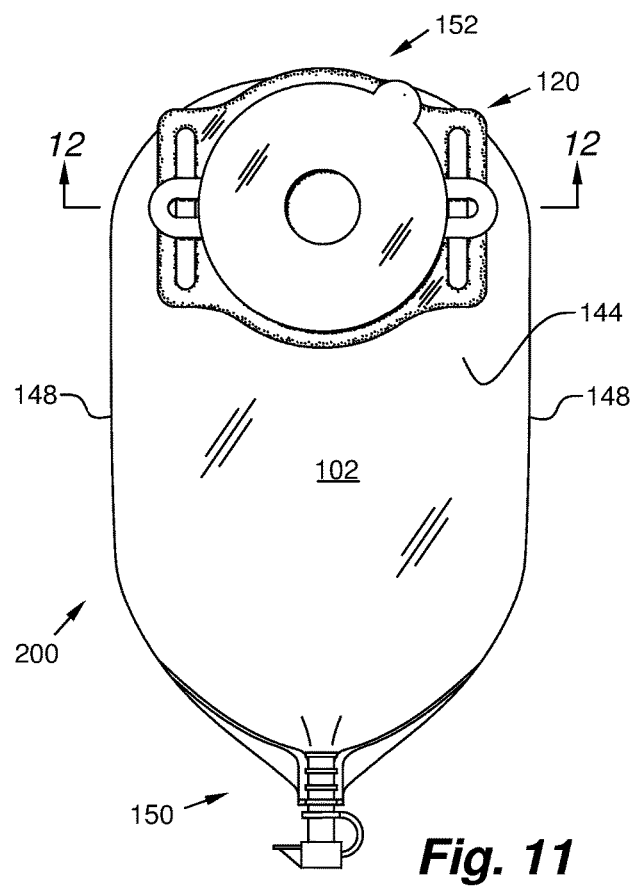
FIG. 11 is a diagrammatic plan view of an exemplary subsequent step to the one or more steps depicted in FIG. 10, showing the upper end of the pouch element having been fed through the junction-engagement aperture, and the belt ring element in mounted engagement with the ostomy pouch subsystem.

Referring to FIG. 11 for example, embodiments of a pouch element 102 may include an inner face 144 to which the junction portion 107 is affixed, an outer face 146 opposite thereof, a pair of lateral sides 148, a lower end 150 and an upper end 152. The lower end 150 typically includes a drainage element 105 thereat. Referring to FIGS. 9-11 for illustration, in a particular preferred embodiment of method of deploying an ostomy support system 100 on a wearer 140, the step of placing may be performed by way of one or more of the following steps. As shown for example in FIG. 9, the lateral sides 148 may be folded toward one another over the outer face 146. The lower end 150 may then be inserted into the junction engagement aperture 128. The belt ring element 120 may be slid toward the upper end 152. As shown for example, in FIG. 10, the upper end 152 may then be fed through the aperture 128, resulting in the configuration depicted, for example, in FIG. 11, wherein the belt ring element 120 is in mounted engagement with the respective ostomy pouch subsystem 200.

Figure 13:
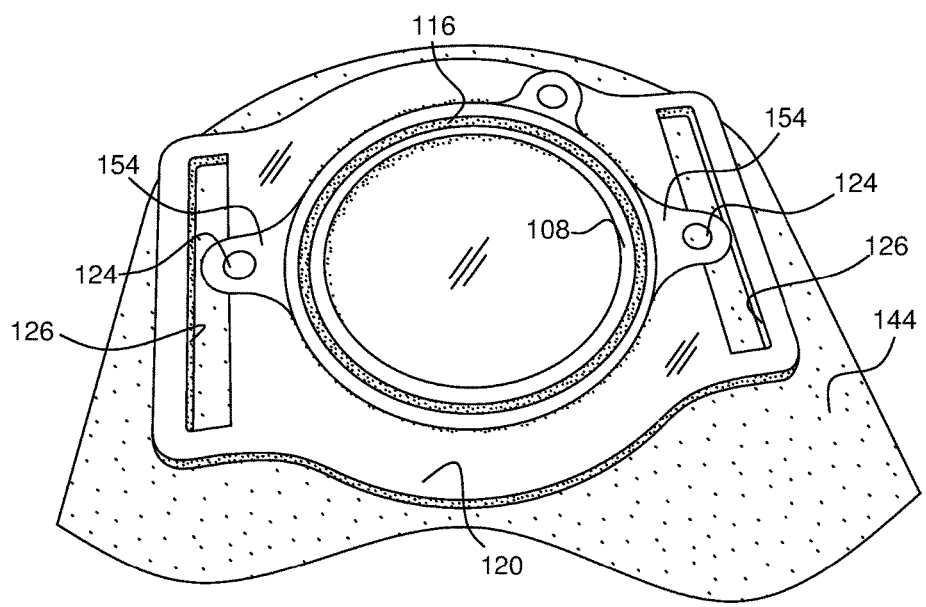
FIG. 13 is a diagrammatic perspective view of a belt ring element in mounted engagement with a partially assembled two-piece ostomy pouch subsystem, the wafer element (not shown here) having been temporarily removed from sealing engagement with the first flange element.

Referring to FIG. 13, an alternative method of placing a belt ring element 120 in mounted engagement with the junction portion of a two-piece ostomy pouch subsystem may involve bending the existing flange loop tabs 154 away from the inner face 144 to allow the belt ring to receive first flange element 108, then allowing the flange loop tabs 154 to return to their original configuration, thereby securing the belt ring in place before the wafer 112 is attached to the first flange element 108.

As illustrated and discussed herein, embodiments of a belt ring element 120 and corresponding belt element 122 in accordance with the present invention may be used to retrofit an existing one-piece or two-piece ostomy pouch subsystem, thus forming an improved overall ostomy system 100.

Referring to FIG. 14 for example, an ostomy pouch subsystem may comprise an ostomy pouch 102 housing an ostomy cavity 104, a pouch inlet aperture 106 in fluid communicating with the ostomy cavity 104, a first flange element 108, an axis 109, a first seal engagement portion 116 (in a two-piece ostomy system) and, in certain embodiments, two or more belt loop portions 124. The wafer subsystem may comprise a base plate or wafer portion 112, a stoma aperture 114, a second flange element 110 and a second seal engagement portion 118 (in a two-piece ostomy system). In a two-piece ostomy system, the first seal engagement portion 116 and second seal engagement portion 118 are typically configured to be press-fit into fluid-sealing engagement with one another, then pulled apart to allow separation of the pouch from the wafer.

Shown generally at 120 are various proposed non-limiting embodiments of a belt ring element in accordance with the present invention. Aperture 128 can take on a multitude of sizes and shapes. As illustrated for example in FIGS. 4-8, the shape of the aperture 128 may be configured to correspond to (e.g., closely match) the size and shape of the outer perimeter of the flange element 108 or weld seal 134 associated with the pouch subsystem. Such corresponding shapes may be circular as illustrated for example in FIGS. 4-7, or in alternative embodiments, may be non-circular, such as polygonal, diamond-shaped, oval, etc. Embodiments in which the respective aperture 128 and weld seal 134 or flange element 108 are correspondingly non-circular may provide further operational advantage by restricting relative rotation 138 between the belt and the pouch, thereby further stabilizing the ostomy system on the wearer 140.

With reference to FIGS. 1 and 13 for illustration, a flange lip or belt loop portions 124 may extend radially outward of the first flange element 108 or wafer, thereby providing a significant degree of axial securement of the belt ring element over the first flange element 108 even before the pouch is attached to the wafer (in a two-piece ostomy system). In a two-piece ostomy system, the belt ring 120 may be further axially retained in its position around the flange once the wafer subsystem has been sealingly secured to the pouch subsystem by way of mutual engagement between first seal engagement portion 116 and second seal engagement portion 118. The belt ring element 120 may preferably be made of a plastic such as, for example, Polypropylene Copolymer or the like.

Figure 3:
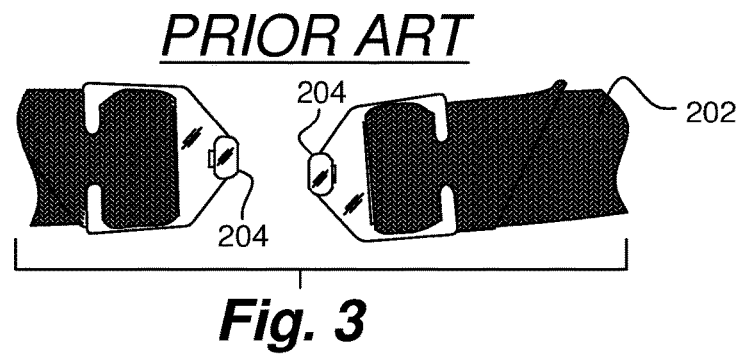
FIG. 3 is a diagrammatic plan view of one example of a pair of prior art ostomy belt ends, including the respective belt loop detents projecting therefrom.

In preferred embodiments, the belt 122 may include hook-and loop fastener surfaces or the like to allow for adjustable securement of the belt through the respective elongated slot(s). Belts of embodiments of the present invention may preferably be formed of an elastic material, and may preferably be approximately 2 inches in width. This is around twice the width of most conventional ostomy belts in use today (such as the prior art belt 202 depicted in FIG. 3), and offers more comfort to the wearer who may use the belt on a daily basis.

The belt ring mounting process illustrated for example in FIGS. 9-11 may be implemented in a one-piece or two-piece ostomy system. Moreover, particular embodiments of the system described herein may also be used as support devices for hernias having protrusions of, for example, approximately 1.5 inches or less.

Certain figures in the present disclosure may include dimensional information. Where this is the case, such dimensional information is provided for illustration only, as it is believed that a routineer in the relevant art, having the benefit of the present disclosure, would be capable of modifying the dimensions shown herein to configure the disclosed invention for use with a variety of ostomy pouch/wafer systems.

Embodiments in accordance to the present invention provide a number of projected advantages over the prior art. By way of example, forces generated between the belt element 122 and flange element 108 or weld joints 134 are no longer principally concentrated at two conventional belt loops 124 (for example, via conventional loop detents 204 shown in FIG. 3), but rather are more broadly distributed around the flange element 108 or weld joint 134. Such improved load distribution significantly reduces the chances of a catastrophic failure of the belt-flange/weld connection, particularly during rigorous activities. Embodiments of the present invention also provide additional support to the abdomen of a wearer directly about the pouch wafer. Further, certain embodiments may support small reducible peristomal hernias. Moreover, embodiments may extend the overall wear time of the pouch/wafer system.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A support retrofit kit for an ostomy pouch subsystem having a pouch element, a wafer element and a junction portion, said kit comprising:
   a belt ring element including a junction-engagement aperture and first and second belt securement portions opposingly disposed laterally of said aperture, said belt ring element configured to being repeatedly placed in and removed from mounted engagement with said ostomy pouch subsystem;
   wherein when said belt ring element is in said mounted engagement, said aperture is in receipt of said junction portion and is axially retained between said pouch element and said wafer element; and
   wherein said junction portion is a weld joint defined by the permanent sealed engagement between said pouch element and said wafer element.

2. A support retrofit kit as defined in claim 1, further comprising an elastic belt element having first and second belt end portions configured for securement to respective said belt securement portions.

3. A support retrofit kit as defined in claim 2 wherein said belt element has a belt width, said belt securement portions each include an elongated slot for receiving said belt element therethrough, and said elongated slots have a slot length which is substantially the same as the belt width.

4. A support retrofit kit as defined in claim 3 wherein said belt slots are parallel to one another and said belt width is between 85% and 100% of said slot length.

5. A support retrofit kit as defined in claim 2 wherein one of said belt end portions is permanently affixed to a respective one of said belt securement portions, and the other said belt end portion is releasably securable to its respective belt securement portion by way of hook and loop fastener surfaces.

6. A support retrofit kit for an ostomy pouch subsystem having a pouch element, a wafer element and a junction portion, said kit comprising:
   a belt ring element including a junction-engagement aperture and first and second belt securement portions opposingly disposed laterally of said aperture, said belt ring element configured to being repeatedly placed in and removed from mounted engagement with said ostomy pouch subsystem;
   wherein when said belt ring element is in said mounted engagement, said aperture is in receipt of said junction portion and is axially retained between said pouch element and said wafer element; and
   wherein said junction portion has a cross-section which is non-circular, and said aperture has a shape which is complementary to said cross-section so as to restrict relative rotation between said belt ring element and said junction portion when said belt ring portion is in said mounted engagement.

7. A support retrofit kit as defined in claim 6 wherein said cross-section is polygonal or oval.

8. A method of deploying an ostomy support system on a wearer, said method comprising the following steps:
   selecting a belt ring element including a junction-engagement aperture, first and second belt securement portions opposingly disposed laterally of said aperture, and a belt element having first and second belt end portions configured for securement to respective said belt securement portions;
   providing an ostomy pouch subsystem having a pouch element, a wafer element and a junction portion, wherein said junction portion is a weld joint defined by the permanent sealed engagement between said pouch element and said wafer element;
   placing said belt ring element in mounted engagement with said ostomy pouch subsystem whereby said aperture is in receipt of said junction portion and said belt ring element is axially retained between said pouch element and said wafer element;
   adhering said wafer element to the skin of said wearer in alignment about a stoma; and
   wrapping said belt element around the torso of said wearer.

9. A method as defined in claim 8 wherein said belt element has a belt width, said belt securement portions each include an elongated slot for receiving said belt element therethrough, and said elongated slots have a slot length which is substantially the same as the belt width.

10. A method as defined in claim 9 wherein said belt slots are parallel to one another and said belt width is between 85% and 100% of said slot length.

11. A method as defined in claim 8 wherein one of said belt end portions is permanently affixed to a respective one of said belt securement portions.

12. A method as defined in claim 8 wherein
   said pouch element includes an inner face to which the junction portion is affixed, an outer face opposite thereof, a pair of lateral sides, a lower end and an upper end; and
   said step of placing is performed by way of at least:
      folding said lateral sides toward one another over said outer face;
      inserting said lower end into said aperture;
      sliding said belt ring element toward said upper end; and
      feeding said upper end through said aperture.

13. A method of deploying an ostomy support system on a wearer, said method comprising the following steps:
   selecting a belt ring element including a junction-engagement aperture, first and second belt securement portions opposingly disposed laterally of said aperture, and a belt element having first and second belt end portions configured for securement to respective said belt securement portions;
   providing an ostomy pouch subsystem having a pouch element, a wafer element and a junction portion;
   placing said belt ring element in mounted engagement with said ostomy pouch subsystem whereby said aperture is in receipt of said junction portion and said belt ring element is axially retained between said pouch element and said wafer element;

adhering said wafer element to the skin of said wearer in alignment about a stoma; and wrapping said belt element around the torso of said wearer;

wherein said junction portion has a cross-section which is non-circular, and said aperture has a shape which is complementary to said cross-section so as to restrict relative rotation between said belt ring element and said junction portion when said belt ring portion is in said mounted engagement.

14. A method as defined in claim 13 wherein said cross-section is polygonal or oval.

* * * * *